(12) United States Patent
Takasu et al.

(10) Patent No.: US 8,808,876 B2
(45) Date of Patent: *Aug. 19, 2014

(54) LIGHT-EMITTING COMPOUND AND ORGANIC ELECTROLUMINESCENCE DEVICE

(75) Inventors: Isao Takasu, Komae (JP); Ryoko Iida, Sunto-gun (JP); Yukitami Mizuno, Tokyo (JP); Shintaro Enomoto, Yokohama (JP); Shuichi Uchikoga, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 478 days.

This patent is subject to a terminal disclaimer.

(21) Appl. No.: 12/616,223

(22) Filed: Nov. 11, 2009

(65) Prior Publication Data

US 2010/0123389 A1    May 20, 2010

(30) Foreign Application Priority Data

Nov. 19, 2008    (JP) ................................ 2008-296051

(51) Int. Cl.
H01L 51/54    (2006.01)

(52) U.S. Cl.
USPC ............ 428/690; 428/917; 313/504; 313/506

(58) Field of Classification Search
None
See application file for complete search history.

(56) References Cited

U.S. PATENT DOCUMENTS

| | | | | |
|---|---|---|---|---|
| 6,023,073 A | * | 2/2000 | Strite | 257/40 |
| 6,034,206 A | * | 3/2000 | Yamamoto et al. | 528/397 |
| 8,053,092 B2 | * | 11/2011 | Miki et al. | 428/690 |
| 2001/0038367 A1 | * | 11/2001 | Inukai | 345/76 |
| 2003/0039858 A1 | * | 2/2003 | Igarashi et al. | 428/690 |
| 2003/0219625 A1 | * | 11/2003 | Wolk et al. | 428/690 |
| 2004/0086745 A1 | * | 5/2004 | Iwakuma et al. | 428/690 |
| 2004/0214036 A1 | * | 10/2004 | Bentsen et al. | 428/690 |

(Continued)

FOREIGN PATENT DOCUMENTS

| | | | |
|---|---|---|---|
| EP | 2282358 | * | 2/2011 |
| JP | 8-60145 | | 3/1996 |

(Continued)

OTHER PUBLICATIONS

Enomoto et al., Digest of Technical Papers—Society for Information Display International Symposium (2009), 40(Bk. 2), pp. 695-698. (Jun. 2009).*

(Continued)

*Primary Examiner* — Dawn Garrett
(74) *Attorney, Agent, or Firm* — Oblon, Spivak, McClelland, Maier & Neustadt, L.L.P.

(57) ABSTRACT

A light-emitting compound includes two or more carbazole skeletons each having two or more fluorine atoms at 2-, 4-, 5- and 7-positions, the carbazole skeleton represented by the formula (1):

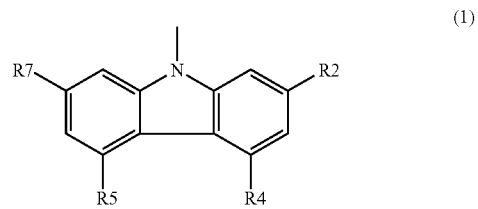

where two or more of R2, R4, R5 and R7 are F and a remainder is H.

6 Claims, 2 Drawing Sheets

(56) References Cited

U.S. PATENT DOCUMENTS

| | | | |
|---|---|---|---|
| 2005/0287396 A1* | 12/2005 | Nakamura et al. | 428/690 |
| 2006/0163562 A1* | 7/2006 | Boerner | 257/40 |
| 2009/0045726 A1* | 2/2009 | Miki et al. | 313/504 |
| 2011/0057180 A1* | 3/2011 | Ono et al. | 257/40 |

FOREIGN PATENT DOCUMENTS

| | | | |
|---|---|---|---|
| JP | 2003-187983 | | 7/2003 |
| JP | 2004-175869 | | 6/2004 |
| JP | 2004-288380 | | 10/2004 |
| SU | 527424 A | * | 7/1977 |
| WO | 03/077609 | | 9/2003 |

OTHER PUBLICATIONS

Moon-Jae Yang et al., "Use of Poly(9-vinylcarbazole) as Host Material for Iridium Complexes in High-Efficiency Organic Light-Emitting Devices", Japanese Journal of Applied Phyiscs, vol. 39, Aug. 1, 2000, pp. L828-L829.

Xiaohui Yang et al., "Highly Efficient Polymeric Electrophosphorescesnt Diodes", Advanced Materials, vol. 18, 2006, pp. 948-954.

U.S. Appl. No. 12/876,632, filed Sep. 7, 2010, Ono, et al.

Japanese Office Action mailed May 8, 2012 in Patent Application No. 2008-296051 with English translation.

* cited by examiner

LIGHT-EMITTING COMPOUND AND ORGANIC ELECTROLUMINESCENCE DEVICE

CROSS-REFERENCE TO RELATED APPLICATIONS

This application is based upon and claims the benefit of priority from prior Japanese Patent Application No. 2008-296051, filed Nov. 19, 2008, the entire contents of which are incorporated herein by reference.

BACKGROUND OF THE INVENTION

1. Field of the Invention

The present invention relates to a light-emitting compound and an organic electroluminescence device.

2. Description of the Related Art

Recently, organic electroluminescence devices (OLEDs) are attracting an attention as a light-emitting technique for next-generation displays and lighting. At the initial stage of the investigation of OLEDs, fluorescence was mainly used as a light-emitting mechanism in an organic layer. However, it is considered that the upper limit of the internal quantum efficiency of fluorescence is 25% in theory. Actually, there was little report which shows a quantum efficiency of more than 25% in OLEDs using fluorescence. On the other hand, it was shown that an internal quantum efficiency of 100% can be obtained in principle in OLEDs using phosphorescence. This is because phosphorescence enables emission of light from excited triplets whereas fluorescence is emitted from only excited singlets and the excited triplets statically exist by thrice as much as the excited singlets. Actually, an experimental result which shows an internal quantum efficiency of approximately 100% was reported in OLEDs using phosphorescence.

A light-emitting layer using phosphorescence has a mainstream structure in which a host material comprising an organic material is doped with a light-emitting metal complex including iridium or platinum as a central metal. One of the mechanisms of generating an exciton for the light-emitting dopant in the phosphorescence light-emitting layer is as follows. Namely, the host material is excited by injection of electrons and holes from an anode and a cathode, the light-emitting dopant is excited by energy transfer from the host material to the light-emitting dopant, and light is emitted during the energy deactivation process from the excited state to the ground state thereof.

As shown in FIG. 1, the larger the overlap (shown by A in FIG. 1) of the emission spectrum of the host material and the absorption spectrum of the light-emitting dopant is, the better the energy transfer efficiency from the host to the light-emitting dopant is. This is called Foerster's energy transfer mechanism.

Host materials for light-emitting layers using phosphorescence are roughly classified into low molecular-type and high molecular-type. A light-emitting layer comprising a low-molecular host material is mainly formed by vacuum co-evaporation of the low-molecular host material and the light-emitting dopant. A light-emitting layer comprising a high-molecular host material is mainly formed by applying a solution mixed with the high-molecular host material and the light-emitting dopant.

Typical examples of the low-molecular host material include p-biscarbazolylphenylene (CBP). Typical examples of the high-molecular host material include polyvinylcarbazole, referred to as PVK (Jpn. J. Appl. Phys., Vol. 39 (2000) pp. L828-L829, and Adv. Mater., 2006, 18, 948-954). The structure and the numbers for the substitution positions of carbazole, and the structure of PVK are shown below.

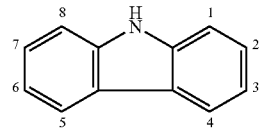

Carbazole (the numerals are the numbers for the substitution positions)

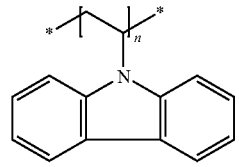

PVK

The light-emitting dopant materials include blue-emitting dopant materials, green-emitting dopant materials, and red-emitting dopant materials. Typical examples of the blue-emitting dopant materials include bis(2-(4,6-difluorophenyl)pyridinate iridium complex [hereinafter referred to as FIrpic]. Typical examples of the green-emitting dopant materials include tris(2-phenylpyridine)iridium complex [hereinafter referred to as Ir(ppy)$_3$]. Typical examples of the red-emitting dopant materials include Bt$_2$Ir(acac).

Here, formation of a light-emitting layer comprising these light-emitting dopant materials and PVK which is a high-molecular host material is envisaged. The emission wavelength of PVK is 420 nm, whereas the absorption band, which is responsible for emission of the light-emitting dopant material, is 380 nm for FIrpic, the blue-emitting dopant material, 410 nm for Ir(ppy)$_3$, the green-emitting dopant material, and 480 nm for Bt$_2$Ir(acac), the red-emitting dopant material. Therefore, for example, where efficient energy transfer from PVK to FIrpic is desired, it is desirable to shift the emission wavelength of PVK toward shorter wavelengths.

Furthermore, a desirable property of the host material for the light-emitting layer using phosphorescence is that the host material does not deactivate the excited triplet state of the light-emitting dopant. For this purpose, it is desirable that the excited triplet energy of the host material is higher than the excited triplet energy of the light-emitting dopant, and thus it is also desirable to shift the emission wavelength of the host material toward shorter wavelengths.

BRIEF SUMMARY OF THE INVENTION

According to an embodiment, there is provided a light-emitting compound comprising two or more carbazole skeletons each having two or more fluorine atoms at 2-, 4-, 5- and 7-positions, the carbazole skeleton represented by the formula (1):

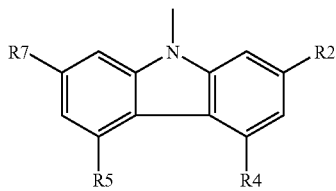

(1)

where two or more of R2, R4, R5 and R7 are F and a remainder is H.

In the light-emitting compound of the embodiment, the compound may be a polymer comprising the carbazole skeletons represented by the formula (1) as repeating units.

According to another embodiment, there is provided an organic electroluminescence device comprising a light-emitting layer between a cathode and an anode, wherein the light-emitting layer comprises a host material of the above light-emitting compound and a blue-emitting dopant.

DETAILED DESCRIPTION OF THE INVENTION

Figure 1:
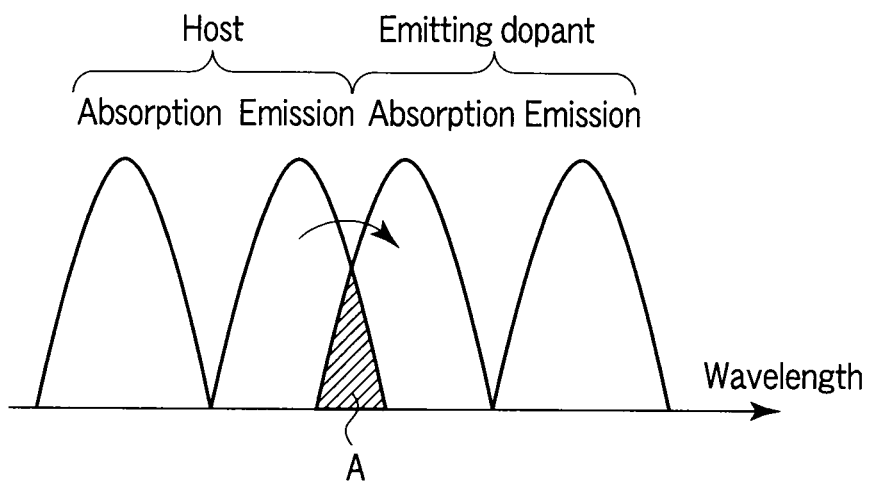
FIG. 1 is a schematic view showing the overlap of the emission spectrum of a host material and the absorption spectrum of a light-emitting dopant.

Hereinafter embodiments of the invention will be described.

The light-emitting compound according to the embodiments comprises two or more carbazole skeletons each having two or more fluorine atoms at 2-, 4-, 5- and 7-positions. Two or more of the substitution positions for fluorine atoms may be arbitrarily selected from 2-, 4-, 5- and 7-positions. It was estimated from molecular orbital calculation that emission is shifted toward shorter wavelengths in such fluorine-substituted carbazole.

Next, a synthetic example of polyvinyl-difluorocarbazole in which 2- and 7-positions of the carbazole skeletons are substituted with fluorine atoms will be described. A reaction scheme is shown below.

(Reaction I)

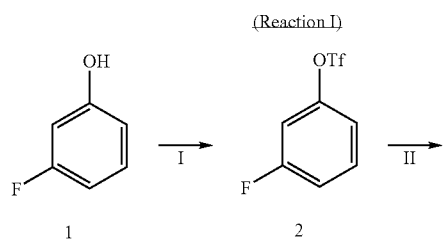

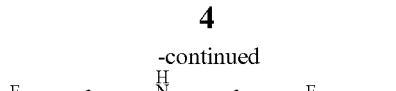

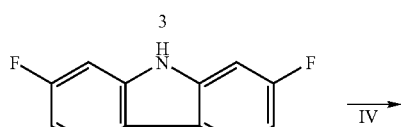

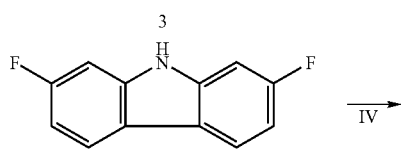

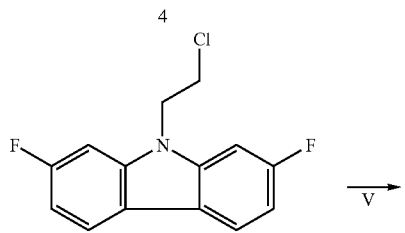

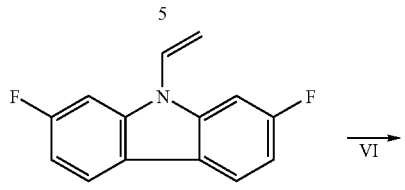

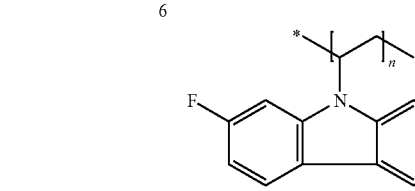

Toluene (50 mL), 3-fluorophenol (1) (25.0 mmol) and a 30% aqueous solution of potassium phosphonate (50 mL) were mixed in a 100 mL three-necked flask. Anhydrous trifluoromethanesulfonic acid (30.0 mmol) was added dropwise under a condition of the reaction liquid of 10° C. or less, and the reaction liquid was stirred under room temperature for 1 hour. The reaction liquid was extracted twice with ethyl acetate (50 mL), washed with water (150 mL), and dried by removing water content with magnesium sulfate to give the liquid compound (2) (23.0 mmol, yield 92%).

(Reaction II)

The compound (2) (2.0 mmol) and 3-fluoroaniline (2.2 mmol) were dissolved in toluene (40 mL). Palladium acetate (0.2 mmol), cesium carbonate (2.4 mmol) and 2-dicyclohexylphosphino-2',4',6'-tri-isopropylbiphenyl (3.0 mmol) as a ligand were added to the reaction liquid, and the reaction liquid was stirred at 100° C. for 2 hours. The reaction liquid was dried in vacuum and the product was isolated by column chromatography (solvent of ethyl acetate:hexane=1:3) to give the compound (3) (1.5 mmol, yield 75%).

(Reaction III)

The compound (3) (4 mmol) and palladium acetate (8 mmol) were added to acetic acid (50 mL) in a 100 mL round-bottom flask, and the reaction liquid was stirred at 100° C. for 4 hours. The reaction liquid was diluted with ethyl acetate, neutralized with an aqueous solution of saturated sodium hydrogen carbonate, and dehydrated with magnesium sulfate. The organic layer was dried in vacuum, and the obtained solid was isolated by column chromatography (solvent of ethyl acetate:hexane=1:3) to give the compound (4) (0.6 mmol, yield 15%). The compound (4) was dissolved in deuterated chloroform to measure a proton NMR spectrum. Chemical shifts at peak positions (ppm): 6.98 (multiplet), 7.09 (quartet), 7.92 (quartet), 8.10.

(Reaction IV)

The compound (4) (3.0 mmol), dimethylsulfoxide (10 mL), potassium hydroxide (9.7 mmol) and chloroethyl tosylate (9.9 mmol) were mixed in a 50 mL round-bottom flask, and the reaction liquid was stirred at room temperature for 5 hours. Ethyl acetate was added to the reaction liquid, and the reaction liquid was washed with water. The solvent was then removed, and the product was dried to give the compound (5).

(Reaction V)

Potassium hydroxide (7.5 mmol), an ethanol solution of the compound (5) (90 mL) and isopropyl alcohol (6.5 mL) were mixed in a 100 mL three-necked flask, heated for 2 hours under reflux, and cooled in a ice bath. Pure water (200 mL) was added to the reaction liquid, and the reaction liquid was filtered. Ethyl acetate was added to the residue, and the residue was dried in vacuum. The product was isolated by column chromatography (silica gel column, solvent of ethyl acetate: hexane=1:5) to give the compound (6) (2.5 mmol, yield 85%).

(Reaction VI)

The compound (6) (2.76 mmol), azobisisobutyro-nitrile (0.38 mmol) and dehydrated tetrahydrofuran (3.3 mL) were stirred at a temperature of 50 to 60° C. for 5 hours in a 50 mL three-necked flask. The reaction liquid was cooled at room temperature, dissolved in tetrahydrofuran, purified by re-precipitation in methanol, and the precipitate was dried to give the compound (7) (517 mg, yield 82%).

The compound (7) was dissolved in deuterated tetrahydrofuran to measure a proton NMR spectrum. As a result, a broad spectrum specific to a polymer was obtained. Chemical shifts at the peak positions (ppm): 2.00, 3.13, 4.70, 6.09, 6.42, 6.65, 7.00, 7.20, 7.436. The number average molecular weight (Mn) was 17,975.

Figure 2:
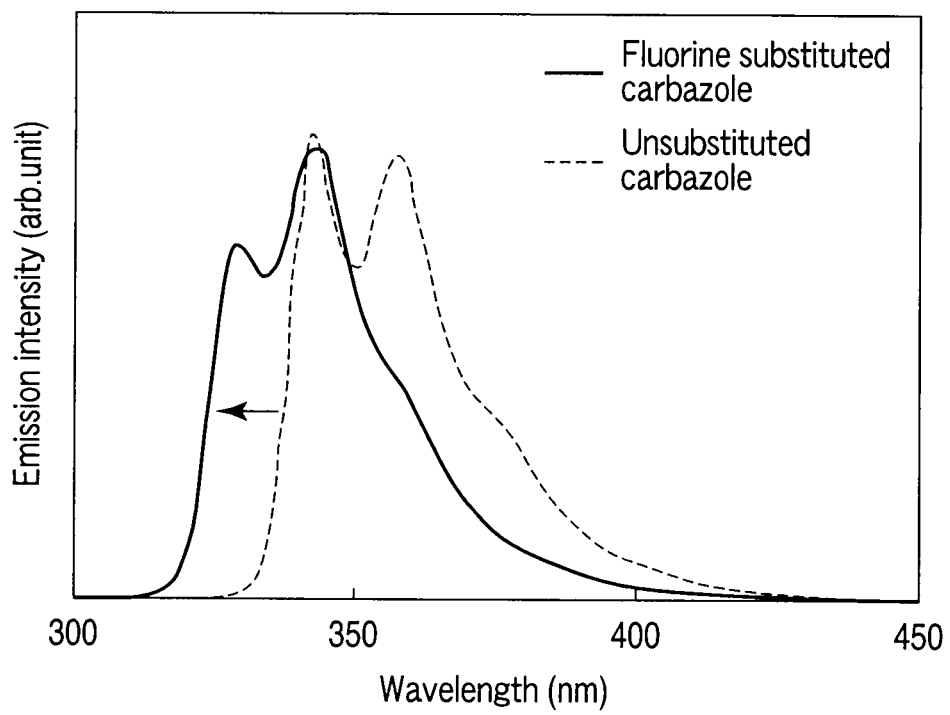
FIG. 2 shows emission spectra of difluorocarbazole and unsubstituted carbazole.

Here, the emission spectra of difluorocarbazole of the compound (4) and unsubstituted carbazole are shown in FIG. 2. As shown in FIG. 2, it is apparent that the emission wavelength is shifted toward shorter wavelengths in difluorocarbazole of the compound (4) as compared to unsubstituted carbazole.

Meanwhile, the following compounds are exemplified as blue phosphorescence light-emitting dopants.

1. Bis(3,5-difluoro-2-(2-pyridyl)phenyl-2-carboxy-pyridyl)iridium

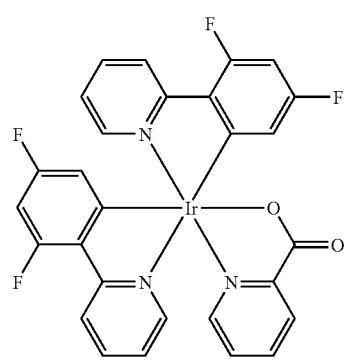

2. Bis(2,4-difluorophenylpyridinato)-tetrakis(1-pyrazolyl)borate iridium

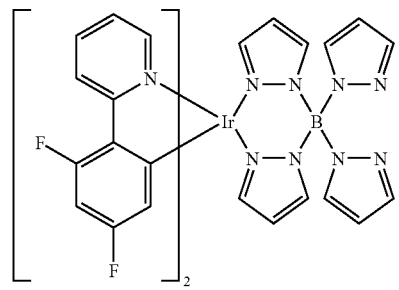

3. Facial iridium(III) tris(1-phenyl-3-methylbenzimidazolin-2-ylidene-C,C2')

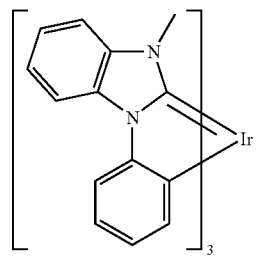

4. Platinum(III) [2-(4,6-difluoro-phenyl)pyridinato-N,C$^2$]-(acetylacetonate)

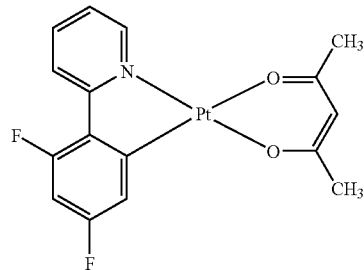

5. Tris(2-(2,4-difluorophenyl)pyridine)iridium(III)

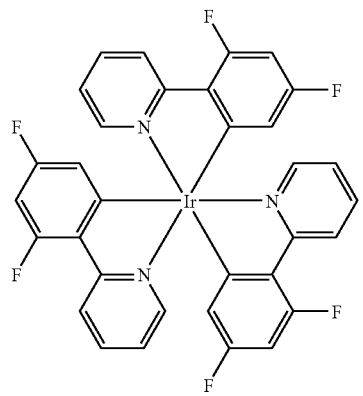

Next, an OLED (Example) having a light-emitting layer comprising the polyvinyldifluorocarbazole (hereinafter referred to as F-PVK) synthesized as above was fabricated.

Figure 3:
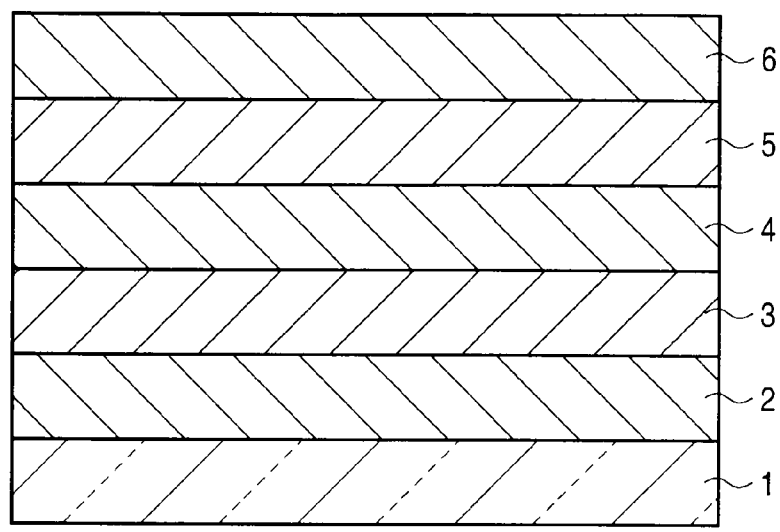
FIG. 3 is a cross-sectional view of the OLED according to an embodiment.

The cross-sectional view of the OLED is shown in FIG. 3. The cathode 2, hole-transport layer 3, light-emitting layer 4, electron-transport layer 5 and electron-injecting layer/anode 6 are formed in this order on the glass substrate 1.

The anode 2 is a transparent electrode of ITO (indium tin oxide) having a thickness of 50 nm. As a material for the hole-transport layer 3, an aqueous solution of poly(ethylenedioxythiophene):poly(styrenesulfonic acid) [hereinafter referred to as PEDOT:PSS] which is an electroconductive ink was used. The aqueous solution of PEDOT:PSS was applied by spin coating, heated and dried to form the hole-transport layer 3 having a thickness of 50 nm.

As materials for the light-emitting layer 4, F-PVK was used as a host material, 1,3-bis(2-(4-tert-butylphenyl)-1,3,4-oxydiazol-5-yl)benzene [hereinafter referred to as OXD-7] was used as a compound which is introduced for the purpose of carrier balancing, and FIrpic was used as a blue phosphorescence light-emitting dopant. These were weighed in a weight ratio of F-PVK:OXD-7:FIrpic=65:30:5 and dissolved in chlorobenzene to give a solution, and the solution was then applied by spin coating, heated and dried to give the light-emitting layer 4 having a thickness of 90 nm.

The electron-transport layer 5 was formed in a thickness of 10 nm by vacuum-evaporating tris(8-hydroxyquinolinato) aluminum [hereinafter referred to as $Alq_3$]. The electron-injecting layer was formed of LiF having a thickness of 1 nm, and an anode was formed of Al having a thickness of 150 nm.

For comparison, an OLED (Comparative Example) was fabricated in a similar manner as described above using unsubstituted PVK as a host material.

Figure 4:
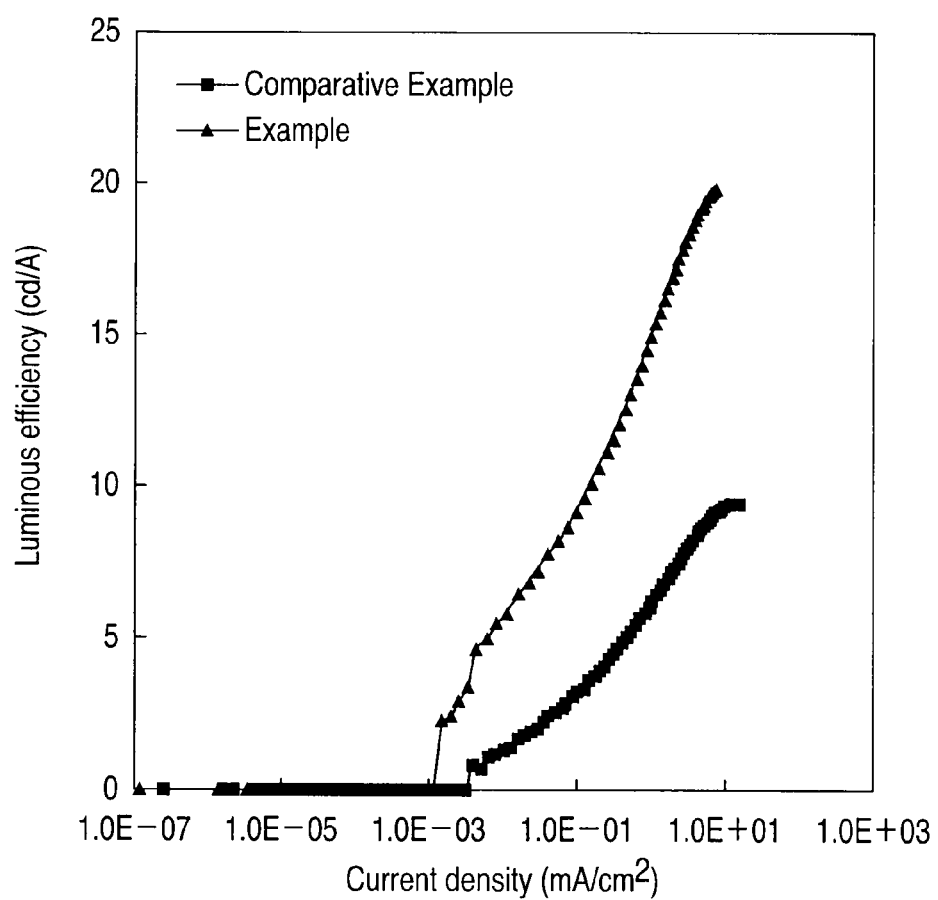
FIG. 4 is a graph showing light-emitting properties of the OLEDs in the Example and Comparative Example.

FIG. 4 shows the emission properties of the OLEDs of the Example and Comparative Example. Both OLEDs exhibited a behavior that emission started in accordance with increase in the current density and the emission efficiency monotonously increased. The OLED of the Example comprising F-PVK in the light-emitting layer had higher emission efficiency than the OLED of the Comparative Example comprising unsubstituted PVK in the light-emitting layer. The highest emission efficiency in the current density range used for measurement was 19.9 cd/A for the Example and 9.3 cd/A for the Comparative Example. This result is attributed to that the emission wavelength was shifted toward shorter wavelengths in the fluorine-substituted F-PVK by which the energy transfer efficiency from F-PVK to FIrpic, the blue-emitting dopant, was improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An organic electroluminescence device, comprising:
   a light-emitting layer between a cathode and an anode,
   the light-emitting layer comprising
      a host material which is a light-emitting compound, and
      a blue-emitting dopant,
   wherein the host material is polyvinylcarbazole comprising a repeating unit comprising a carbazole skeleton having two fluorine atoms located at 2- and 7-positions, represented by the following formula:

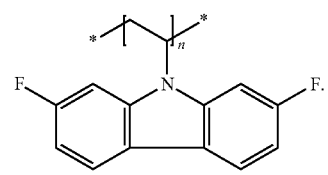

2. The organic electroluminescence device according to claim 1, wherein said blue-emitting dopant is a bis(2-(4,6-difluorophenyl)pyridinate iridium complex.

3. The organic electroluminescence device according to claim 1, wherein said blue-emitting dopant is at least one member selected from the group consisting of bis(3,5-difluoro-2-(2-pyridyl)phenyl-2-carboxypyridyl)iridium, bis(2, 4-difluorophenylpyridinato)-tetrakis(1-pyrazolyl)borate iridium, facial iridium(III) tris(1-phenyl-3-methylbenzimidazolin-2-ylidene-C,C2'), platinum(III) [2-(4, 6-difluoro-phenyl)pyridinato-N,$C_2$]-(acetylacetonate) and tris(2-(2,4-difluorophenyl)pyridine)iridium(III).

4. The organic electroluminescence device according to claim 1, further comprising, in said light emitting layer, 1,3-bis(2-(4-tert-butylphenyl)-1,3,4-oxydiazol-5-yl)benzene as a carrier balancing compound.

5. The organic electroluminescence device according to claim 1, comprising:
   a glass substrate,
   said cathode,
   a hole-transport layer,
   said light-emitting layer,
   an electron-transport layer, and
   said anode.

6. The organic electroluminescence device according to claim 5, comprising, in order, said glass substrate, said cathode, said hole-transport layer, said light-emitting layer, said electron-transport layer, and said anode.

* * * * *